United States Patent [19]

Newton et al.

[11] 4,255,088
[45] Mar. 10, 1981

[54] LIQUID PUMPING SYSTEM HAVING MEANS FOR DETECTING GAS IN THE PUMP

[75] Inventors: David W. Newton, Boulder, Colo.; John M. Gibilisco, Cedar Rapids, Iowa

[73] Assignee: Valleylab, Inc., Boulder, Colo.

[21] Appl. No.: 48,380

[22] Filed: Jun. 14, 1979

[51] Int. Cl.³ .............................................. F04B 49/00
[52] U.S. Cl. ........................................... 417/1; 73/19
[58] Field of Search ................ 417/1, 22, 38; 73/19, 73/53

[56] References Cited

U.S. PATENT DOCUMENTS

| 2,406,179 | 8/1946 | Waish et al. ............................. 73/19 |
| 2,765,743 | 10/1956 | Hollinshead . |
| 3,559,644 | 2/1971 | Stoft et al. . |
| 3,847,507 | 11/1974 | Sakiyama et al. ...................... 417/22 |
| 3,855,515 | 12/1974 | Hutchins ............................ 417/44 X |
| 3,981,620 | 9/1976 | Abrahams ............................ 417/42 |
| 4,137,011 | 1/1979 | Rock ...................................... 417/22 |

Primary Examiner—Edward L. Roberts
Attorney, Agent, or Firm—Gerald J. Ferguson, Jr.; Joseph J. Baker

[57] ABSTRACT

An improved liquid pumping system wherein gas within the pump may be detected to indicate an error in desired flow rate or displaced volume. The system may be shut down if excessive gas is detected in the pump. Further, the flow rate may be corrected to the desired rate.

24 Claims, 7 Drawing Figures

LIQUID PUMPING SYSTEM HAVING MEANS FOR DETECTING GAS IN THE PUMP

BACKGROUND OF THE INVENTION

This invention relates to liquid displacement pumps and the like and, in particular, to means for controlling the delivery rate thereof.

When pumping liquids in certain fields, the flow rate thereof can be critical. Illustrative of such fields are the pumping of physiological liquids in the medical field and the pumping of liquids in liquid chromatography systems. In the medical field, infusion pumps are employed where the liquid is precisely metered into a patient's circulatory system. It is typical in these systems to set a predetermined flow rate at which fluid is delivered, it being assumed that the fluid will indeed be delivered at the desired rate. However, if gas is present in the pump, the flow rate will typically be less than that required.

SUMMARY OF THE INVENTION

It is thus a primary object of this invention to provide an improved liquid pumping system wherein gas within the pump may be detected to indicate an error in the desired flow rate.

It is a further object of this invention to provide an improved pumping system of the above type where the system is shut down and user alerted if excessive gas is detected in the pump.

It is a further object of this invention to provide an improved fluid pumping system of the foregoing type where the flow rate may be corrected to the desired rate in the event gas is present in the pump.

Other objects and advantages of this invention will be apparent from a reading of the following specification and claims taken with the drawing.

DETAILED DESCRIPTION OF THE PREFERRED EMBODIMENTS OF THE INVENTION

Figure 1:
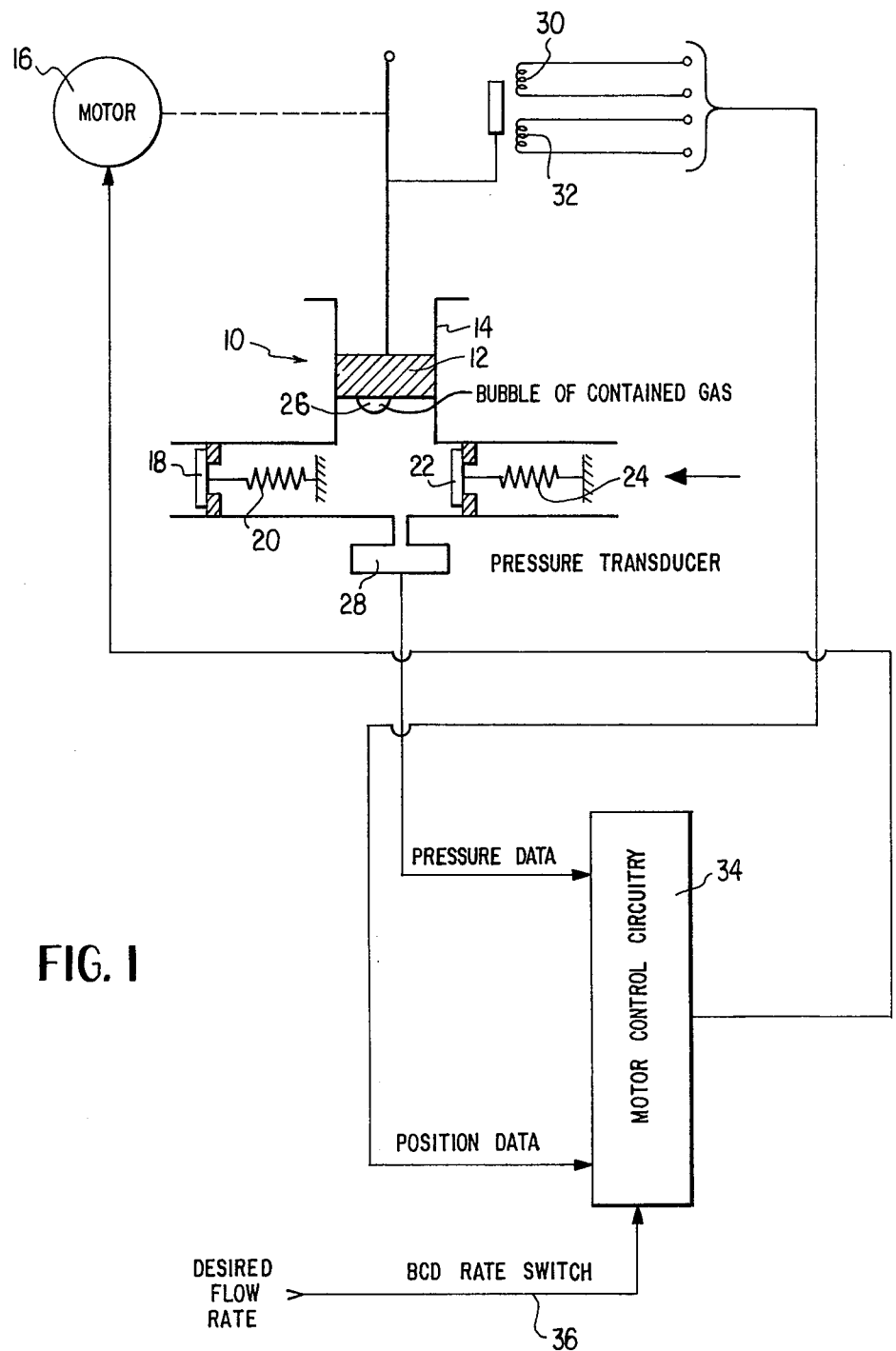
FIG. 1 is a combined diagrammatic and block diagram of an illustrative liquid pumping system in accordance with the invention.

Reference should be made to the drawing where like reference numerals refer to like parts.

In FIG. 1, a pumping system in accordance with the invention is shown. A pump 10 is of the liquid displacement type which typically employs a piston 12 slidably disposed within a cylinder 14. The piston is driven by a motor 16, which typically is a brushless D.C. motor. Check valves 18 and 22 with associated springs 20 and 24 are typically employed whereby valve 18 opens to permit liquid delivery during downward movement of the piston and valve 22 opens to permit refill of the pump chamber during upward movement of the piston. As is typical with such a displacement pump and similar type pumps, the fluid is restrained from flowing either from or to the pump chamber for a portion of the pump cycle, this being accomplished by the check valves 18 and 22 in the illustrative embodiment of FIG. 1. As will be described in more detail hereinafter, it is while the pump is in the aforementioned sealed state, that pump pressure and pump volume change are sensed and processed to yield compressibility data. Low compressibility is indicative of the absence of gas in the pump chamber since gas is compressible while the liquid which is to be pumped is not compressible. High compressibility is indicative of the presence of gas. A bubble of contained gas is indicated at 26 and can undesirably cause the liquid delivery rate to be less than that set for the pump.

Figure 6:
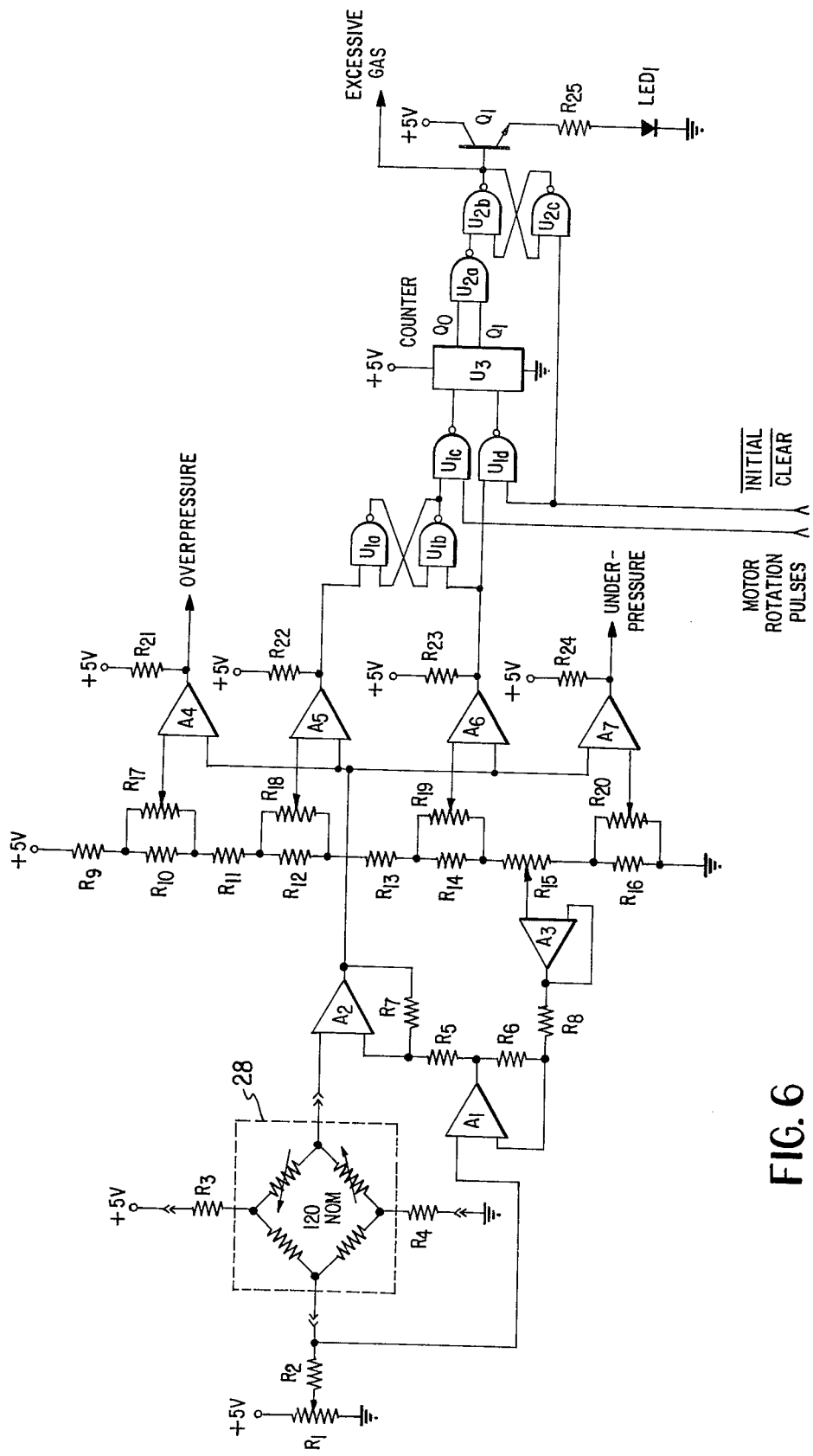
FIG. 6 is a schematic diagram of the gas detector circuitry of FIG. 3.

In order to obtain the pump pressure data, a pressure transducer 28, which may be of a conventional type such as that illustrated in FIG. 6, is connected to the chamber of pump 10. In order to obtain the pump volume change data, advantage may be taken of the fact that the lower surface area of piston 12, of course, remains constant over a pump cycle. Hence, the volume change is a function of piston position. As will be described hereinafter, any signal proportional to this position may be employed such as pulses derived from a photo optical shaft encoder 30 or from the output of an LVDT 32.

The pump pressure data and piston position data is applied to motor control circuitry 34, the purpose of which is to control motor 16 and thus, the delivery rate of pump 10. The desired liquid delivery is applied over line 36 and it is this rate which can be in error due to the presence of gas bubble 26 in the pump chamber.

Figure 2:
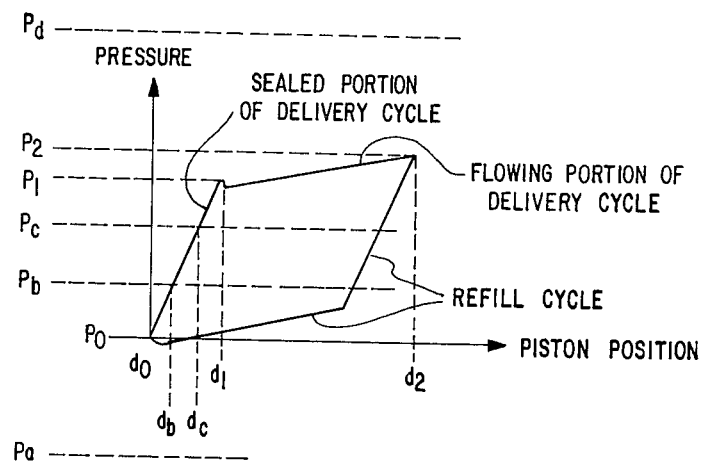
FIG. 2 is a pump pressure-piston position trace of an illustrative pump cycle of the system of FIG. 1.

Referring to FIG. 2, there is shown an illustrative pump pressure-piston position trace. During the delivery portion of a pump cycle, the pump piston moves from a raised position (in the example of FIG. 1), indicated at $d_0$, to a lowered position $d_2$ while the pressure increases from $p_0$ to $P_2$. During the pressure increase from $p_0$ to $p_1$, the pump chamber is sealed. It is during this time that the compressibility data is obtained, as will be discussed hereinafter with respect to FIG. 6. From $p_1$ to $p_2$, the liquid is delivered from the pump chamber, after which the chamber is refilled as the piston retracts from $d_2$ back to $d_0$.

Figure 3:
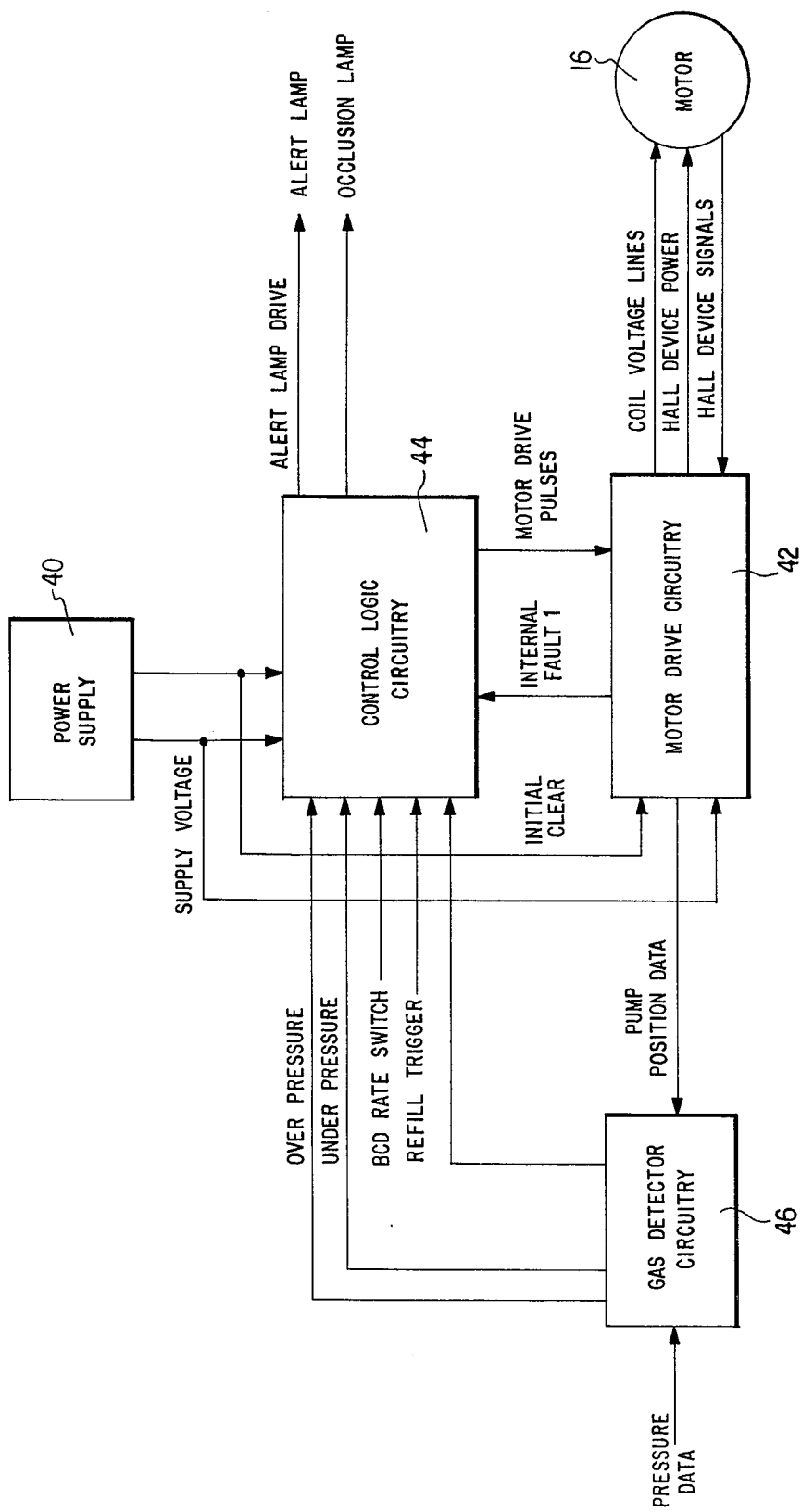
FIG. 3 is a block diagram of the motor control circuitry of FIG. 1.

FIG. 3 is a block diagram of illustrative motor control circuitry 34 of FIG. 1, which includes power supply 40, motor drive circuitry 42, control logic circuitry 44 and gas detector circuitry 46 where circuits 40, 42 and 44 are incorporated in a pumping system (the IV5000 Pump) presently sold by the assignee of this application—that is, Valleylab, Inc. of Boulder, Colo. Circuitry 34 accepts inputs supplied via operator actuated controls as well as those generated within the electromechanical system and outputs signals to the windings of motor 16 and alert indicator lamps, an alert tone speaker, and a nurse call jack (the latter three components not being shown).

Figure 4:
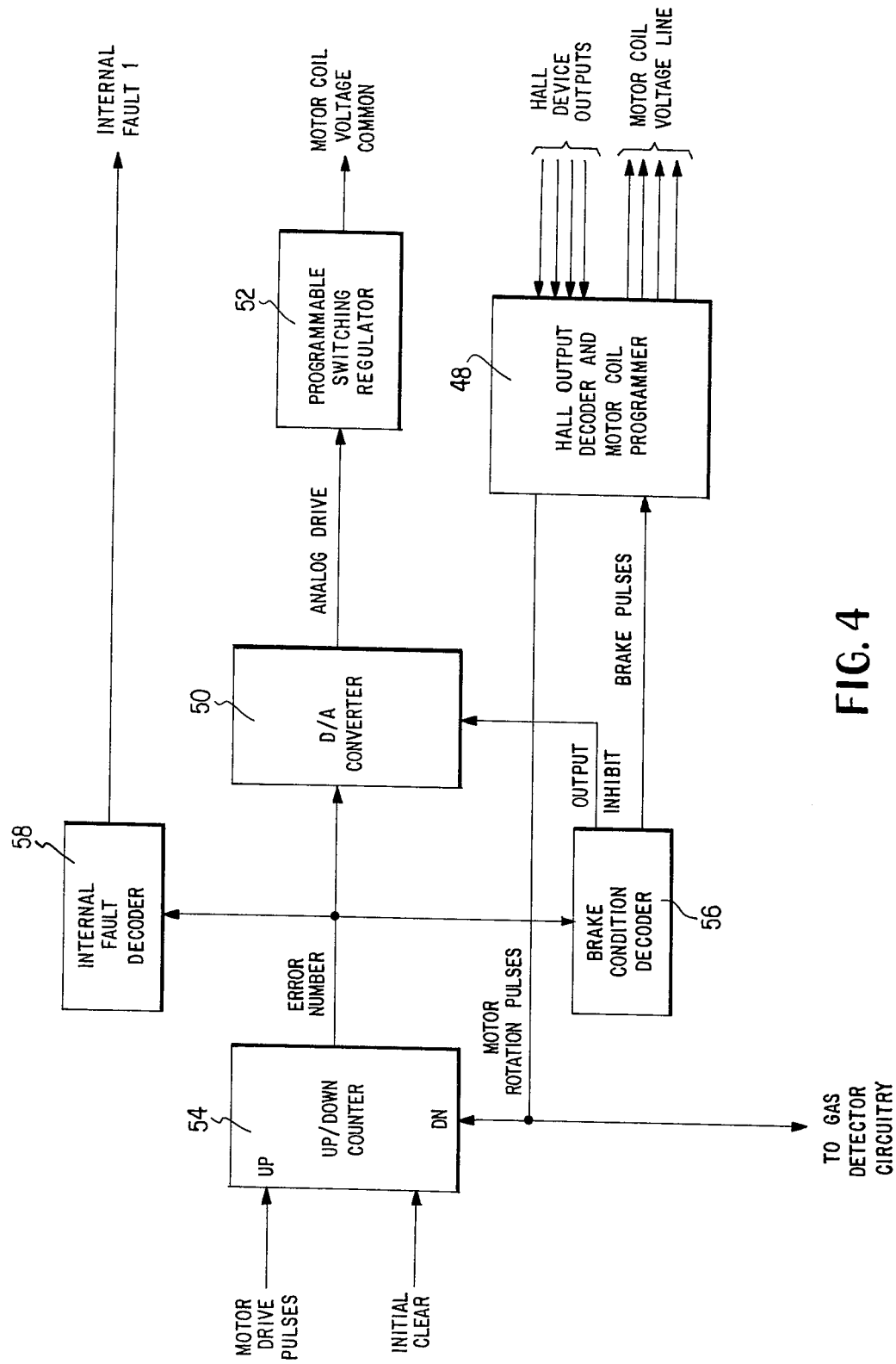
FIGS. 4 and 5 are respective block diagrams of the motor drive circuitry and the control logic circuitry of FIG. 3.

FIG. 4 is a block diagram of illustrative motor drive circuitry 42. Hall Effect devices in the motor provide coil sequencing information as well as incremental shaft position information to the motor circuits. A Hall output decoder and motor coil programmer 48 decodes Hall output waveforms to generate two Motor Rotation Pulses per revolution of the motor. A servo-system is provided using these pulses as feedback. The forward loop of the system consists of a D/A converter 50 which drives a programmable switching regulator 52, which in turn supplies voltage drive to motor 16. A digital error input to D/A converter 50 causes a motor voltage output. An up/down counter 54 provides the error signal. Motor Drive Pulses at the up count input give a positive error signal to the system; Motor Rotation Pulses at the down count input reduce the error number. An Initial Clear Pulse clears the counter at unit turn on.

Under normal operation an equilibrium error number is maintained for a given rate of input drive pulses. Increasing the input rate of pulses will increase the equilibrium error number, and therefore, the voltage level supplied to the motor. Motor speed will track the input rate of Motor Drive Pulses. Since two counts are subtracted from the error number with each revolution of the motor, each Motor Drive Pulse input advances the motor exactly one-half revolution. The incremental motion of the motor is thus determined exactly by the total number of input pulses to the system.

Motor drive is unidirectional since a negative count does not reverse motor direction. Thus, a negative count is decoded by a brake condition decoder 56 as a brake condition—that is, the motor has rotated beyond the number of rotations given by the input pulses. At the first negative count, the Brake Pulse causes all motor coils to be energized for a short time after which an inhibit is supplied to the D/A output preventing further motion of the motor until the error number is again positive. If the motor rotation speed does not keep up with the motor drive pulse rate, the error count will not reach equilibrium. In this case a maximum error number is detected and interpreted as a system failure. An Internal Fault Decoder 58 supplies this information to control logic circuitry 44 via the Internal Fault 1 output.

Figure 5:
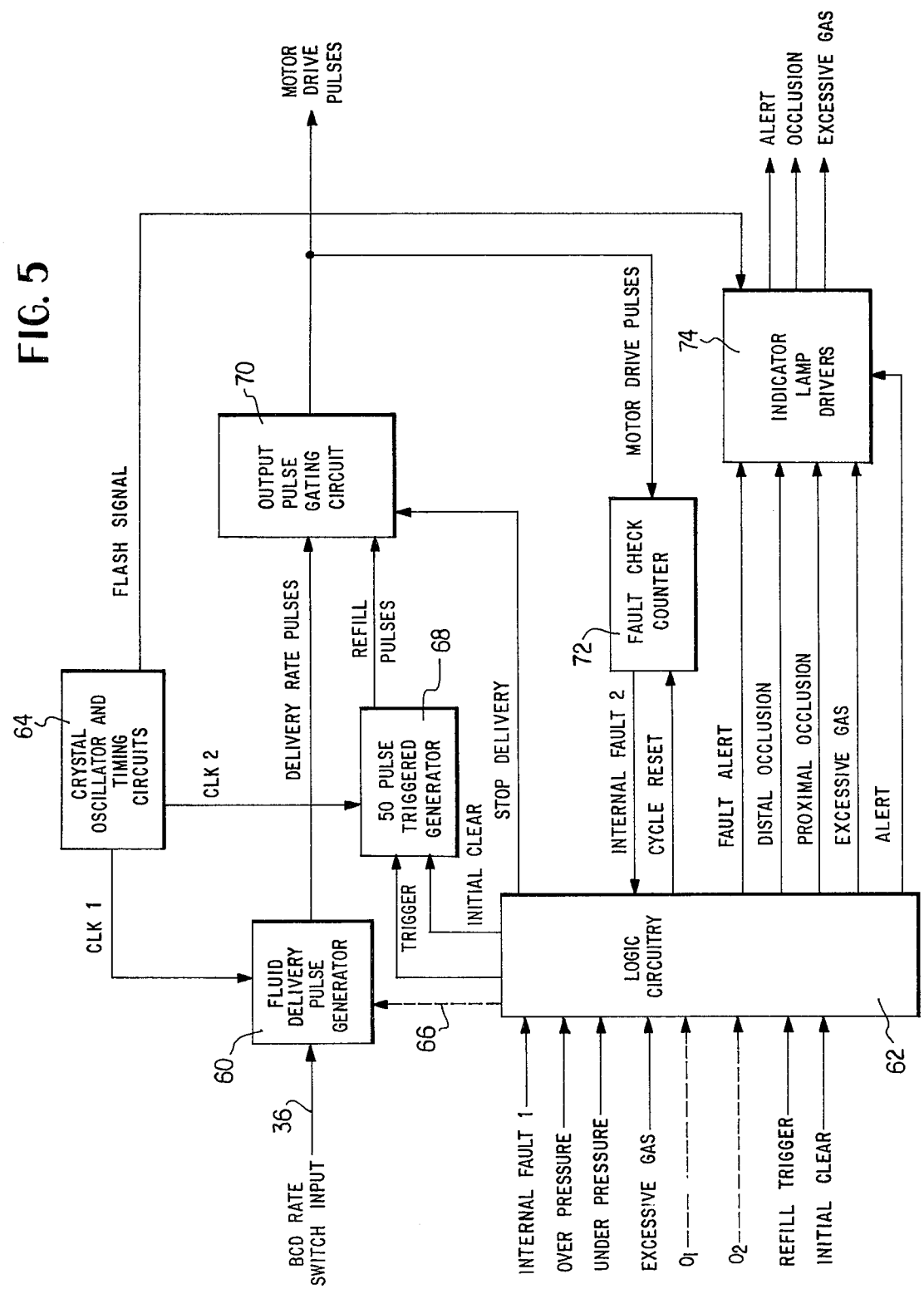

FIG. 5 is a block diagram of control logic circuitry 44. In general, the functions of this portion of the electronics may be summarized as follows: (1) generate Motor Drive Pulses whose rate is proportional to the infusion rate number which is set on the BCD Flow Rate Selector; (2) activate the proper alert indicator lamps for the various conditions which are monitored via logic inputs supplied from the electromechanical system; and (3) transmit either Infusion Rate or no pulses to motor drive circuitry 42 depending upon monitor logic inputs present.

A first logic input to the control logic circuitry 44 is a flow rate selector switch (not shown) which is connected to line 36. The flow rate selector switch, a three digit thumbwheel switch, is located on the front panel. The output of the switch is a digital BCD code of the set number typically indicating infusion rate in ml/hr and is, in particular, applied to a fluid delivery pulse generator 60, which will be described in more detail hereinafter. The flow rate setting may be limited mechanically to the range 000. to 499. ml/hr.

Overpressure, Underpressure and Excessive Gas signals are generated by gas detector circuitry 46 and also applied to control logic circuitry 44 and, in particular to logic circuitry 62. If in the process of pumping, the positive pressure in the pump chamber exceeds the preset limit, $P_d$ in FIG. 2, the Overpressure signal is generating thereby signaling a distal line occlusion. Likewise, if while pumping, the negative pressure in the pump chamber exceeds the preset lower limit, $P_a$ in FIG. 2, the Underpressure signal is generated, signaling a proximal line occlusion (empty bottle). If excessive gas is present in the pump chamber, the Excessive Gas signal is generated. Further, as will be discussed hereinafter with respect to FIG. 7, the amount of gas detected in the pump chamber can be utilized to correct rate errors due to gas by varying the displacement rate. Inputs $O_1$ and $O_2$ to logic circuitry 62 are employed for this purpose.

A Refill Trigger signal is generated by the momentary closure of a microswitch (not shown) that is actuated once every pump cycle in the aforesaid IV 5000 Pump. This signal occurs at the end point of the outward motion of pump 10 and is applied to control logic circuitry 44. At this point, the electronic mechanism speeds up for quick refilling of the pump. An Initial Clear signal is generated in power supply 40 whenever unit power is turned on. The purpose of this signal is to clear all counters and latching logic in the system. The Internal Fault signal is generated by internal fault decoder 58 of Motor Drive Circuitry 42. This feedback input indicates a system failure in that the motor speed is not tracking the Motor Drive Pulse rate being delivered.

Infusion rate accuracy is maintained through the use of a crystal oscillator 64 with a typically better than 0.01% overall frequency accuracy. The crystal frequency of typically 2.275556 MHz. drives 25 stages of binary countdown. These counter outputs are decoded to generate the various timing signals required. Clk1 and Clk2 are master clocks of the same frequency (69.445 Hz.) but opposite phase. A Flash Signal for the indicator lamps is a square wave at 1.085 Hz.

The pump cycle is partitioned into two sections: fluid delivery stroke and pump refill stroke. During each cycle, one-half cycle of the pump is required for the delivery stroke and one-half cycle for the refill stroke. In the delivery stroke, the motor speed is controlled by whatever flow rate is selected. In the refill stroke, the motor is maintained at a constant speed which is approximately twice the fastest delivery stroke speed. A gear reduction (not shown) at the motor output sets the number of pulses required for each pump cycle at 100.

Fluid delivery pulse generator 60 comprises a series of BCD rate multipliers which accept the Flow Rate Selector BCD numbers and Ck1 pulses as inputs. Depending on whether $O_1$ or $O_2$ are logical true, a BCD input may also be applied over dashed line 66. The output is a pulse train whose rate is proportional to the BCD input. The flow rate pulse frequency is set so that exactly 50 pulses are delivered in the time required for the fluid delivery stroke of the pump cycle at any given infusion rate input.

A 50 pulse triggered generator 68 supplies the remaining drive pulses during the pump refill stroke. Upon a trigger to generator 68, a burst of 50 Ck2 pulses is gated to its output. The Trigger signal is supplied once per pump cycle via the Refill Trigger Signal. The combination of 50 Delivery Rate Pulses and 50 Refill (Ck2) pulses drive the pump one complete cycle. Repetition rate of the pump cycle is thus achieved as a function of Flow Rate Selector setting and the input on line 66.

An Output Pulse Gating Circuit 70 transmits a combination of Delivery Rate Pulses and Refill Pulses (collectively Motor Drive Pulses) to Motor Drive Circuitry 42 depending on the condition of the Stop Delivery input. A true condition on the Stop Delivery input inhibits transmission of normal Delivery Rate and Refill Pulses.

Logic Circuitry 62 supplies control signals required for output pulse gating as well as alert indication. Particular output signals generated are: (1) Stop Delivery which is logical true for true conditions of Overpressure, Underpressure, Internal Fault 1, Internal Fault 2 or Excessive Gas; (2) Fault Alert, which is true if either Internal Fault 1 or Internal Fault 2 are true; (3) Distal Occlusion, which is true when the Overpressure input is true; (4) Proximal Occlusion, which is true when the Underpressure input is true; (5) Excessive Gas output, which is true when the Excessive Gas input is true; (6) Alert Signal, which is true for all of the Stop Delivery conditions; and (7) Cycle Reset, which is true coincident with a Refill Trigger input or whenever the Initial Clear Pulse is supplied. While the system is pumping, the Cycle Reset signal occurs once per cycle.

All outputs occurring for Overpressure, Underpressure, Excessive Gas and Internal Fault conditions are latched and cannot be removed unless unit power is turned OFF and then ON again so that the Initial Clear pulse is supplied.

An Internal Fault Check Counter 72 is a binary up counter which counts the number of pulses transmitted to motor drive circuitry 42 during a pump cycle. The counter is cleared by the Cycle Reset signal. Average count per cycle should be 100. If the Refill Trigger is not being supplied to the logic circuitry, (i.e. pump not pumping, Refill Switch not functioning, or Motor Drive Pulses not being counted by the motor drive circuitry 42) the count will continue to accumulate. A maximum count of 128 is detected as a system failure and Internal Fault 2 signal is supplied to the logic circuitry 62.

Indicator lamp drivers 74 supply power to the Alert and Occlusion Indicator lamps (not shown) as a function of the input conditions present. Alert Indicator power is supplied continuously whenever the Alert input is true and the Fault Alert input is not true. When both Alert and Fault Alert are true, the Alert Indicator power is controlled by the Flash Signal which is supplied from Timing Circuit 64. Occlusion Indicator power is supplied continuously if the Alert and Distal Occlusion inputs are true. When the Alert and Proximal Occlusion inputs are true, Occlusion Indicator power is controlled by the Flash Signal. Excessive Gas Indicator power may be supplied either continuously or under the control of the Flash Signal when the Excessive Gas and Alert inputs are true. Alert input is always true if either Occlusion or the Excessive Gas input is true, or if the Keep Open input (not shown) is true.

Illustrative gas detector circuitry 46 together with illustrative pressure transducer 28 is shown in FIG. 6. Basically, circuitry 46 obtains compressibility data by determining the change of pump pressure with respect to change in pump volume to thus determine the amount of gas, if any, present in pump 10.

Pressure transducer 28 may be a resistance-bridge where the resistors shown as variable change with pressure, this being a typical transducer network where any of a large variety of transducers can be used. Three interconnected amplifiers $A_1$, $A_2$ and $A_3$ are equivalently a single high grade instrumentation operational amplifier.

Resistors $R_1$ and $R_{17}$-$R_{20}$ are trip level adjustments for pressure comparators $A_4$, $A_5$, $A_6$, $A_7$. $R_{17}$-$R_{20}$ are individual adjustments and $R_1$ affects all points. Only two adjustments are also possible—that is, gain and zero with the interrelationship among the trip pressures defined by precision resistors alone. Comparators $A_4$-$A_7$ trip at pressures $P_a$-$P_d$ respectively, the latter pressures being shown in FIG. 2. $A_4$ and $A_7$ are the limit under and over pressures respectively, and are not involved with gas detection per se.

Pressures $P_b$ and $P_c$ fall within the sealed-system slope discussed hereinbefore with respect to FIG. 2. The logic is arranged so that counter $U_3$ counts line pulses between $P_b$ and $P_c$. These can be any signals or pulses proportional to pump piston position. In the present embodiment, they are the Motor Rotation Pulses, which are counted via NAND gate $U_{1c}$. They could be pulses from photo optical shaft angle encoder 30 or pulses derived from the output of LVDT 32.

Counter $U_3$ commences counting the Motor Rotation Pulses when the output from $A_2$ exceeds the reference potential established by potentiometer $R_{19}$ to thereby switch the output of $A_6$ and reset latch $U_{1a}$, $U_{1b}$ so that $U_{1c}$ is conditioned to pass the Motor Rotation Pulses to $U_3$. When the output from $A_2$ exceeds the reference potential established by potentiometer $R_{18}$ to thereby switch the output of $A_5$, latch $U_{1a}$, $U_{1b}$ is set by the switched output of $A_5$ to thereby prevent further application of the Motor Rotation Pulses of $U_3$. Hence, the count of $U_3$ is indicative of the slope of the line representing the sealed portion of the pump delivery cycle as shown in FIG. 2. That is, the number of Motor Rotation pulses which occur between $d_b$, the piston position at pressure $P_b$, and $d_c$, the piston position at pressure $P_c$, is indicative of the slope of the sealed portion line, as can be seen in FIG. 2. Hence, it is also representative of the amount of gas in the pump chamber. The output of $U_3$ is read by NAND gate $U_{2a}$ which may, for example, be sensitive to the binary number 11 (decimal 3). When 11 is detected, output latch $U_{2b}$, $U_{2c}$ is set and the Excessive Gas signal is generated to thereby stop the system although this signal does not necessarily have to stop the system. Rather, only an Excessive Gas lamp may be illuminated, this being indicated as $LED_1$ in FIG. 6. Reset occurs when $\overline{INITIAL\ CLEAR}$ is activated (driven to logic zero). This occurs when the power switch is turned off then on again.

Figure 7:
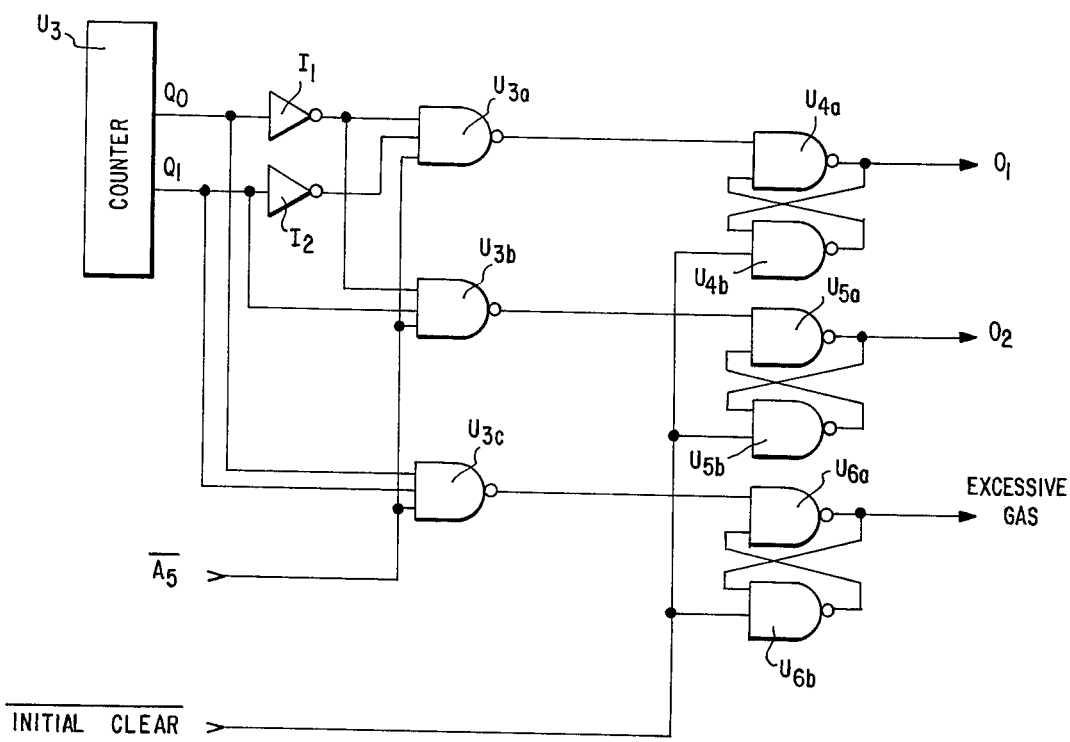
FIG. 7 is a schematic diagram of a modification of the gas detector circuitry of FIG. 6.

The circuitry of FIG. 7 is a modification of the circuitry of FIG. 6, which corrects the fluid displacement rate due to the presence of air (or gas) assuming there are typical pumping pressures. This circuitry is connected to $U_3$ in place of that employed in FIG. 6. There are four states of the output. First, there may be no output; not even a single pulse is counted by $U_3$ between $P_b$ and $P_c$, thus the pump contains only a very small amount of gas and no action is taken. The second output is $O_1$. One pulse is counted between $P_b$ and $P_c$ and a slight increase in stroke rate is required to correct for air contained in the pump. In particular, the output of $U_3$ is 01 which is detected by inverters $I_1$ and $I_2$, NAND gate $U_{3a}$ and latch $U_{4a}$, $U_{4b}$ to provide the $O_1$ output.

The third output of the FIG. 7 circuitry is $O_2$. Two pulses are counted between $P_b$ and $P_c$, and a large increase in stroke rate is required to compensate for gas in the pump. In this state, a 10 output from $U_3$ is detected by NAND gate $U_{3b}$ and latch $U_{5a}$, $U_{5b}$ to provide the $O_2$ output. The last output is the Excessive Gas output where three pulses are counted between $P_b$ and $P_c$. Thus, there is too much air for successful operation and the system may be shut down and an alert issued. Here, the 11 output of $U_3$ is detected by NAND gate $U_{3c}$ and latch $U_{6a}$, $U_{6b}$.

The foregoing system is illustrative only. Different detected counts may be selected with perhaps a greater number of counts required to trip the $O_1$ state and different ratios of counts between $O_1$, $O_2$ and Excessive Gas. Two states or more than three may be used.

Changes can occur in the pressure baseline, this corresponding to pressure $P_0$ in FIG. 2. In particular, the baseline can change with variations in (a) input and/or output valve pressure drops, (b) input head pressure or (c) output head pressure. It is possible to sweep the midpoint of $P_b$ and $P_c$ over some expected range and look for the minimum count (maximum slope) over the sweep range, although this would substantially increase hardware complexity. In any event, the present embodiment of the invention gives usable information for many applications including the use in a medical infusion pump.

One feature which may be useful is the examination for stroke to stroke repeatability. The reason for this is that during initial set-up the input and/or output head pressure may be different from the steady state value. As previously mentioned, this could cause a baseline shift which could throw the system off the proper portion of the pressure-position loop. Since the anticipated slope is normally the steepest slope, this kind of behavior would normally result in the detection of a less-steep slope (more counts) and possibly a false detection of contained gas. Several corrections are possible. First, there may be obtained an N stroke running average of slope possibly with initially expanded sensitivity so that during the first few strokes gross errors would be detected, but smaller baseline discrepancies would be ignored. During the subsequent strokes, the sensitivities would gradually increase to the final value. Next, the first M strokes may be ignored on the air detector output. Finally, a requirement may be made that at least a certain number of strokes have the same output from the air detection/correction network.

What is claimed is:

1. Liquid pumping apparatus comprising
   a pump for pumping a liquid; and
   gas detecting means disposed in the pump for detecting within said pump the presence of gas which may undesirably affect the liquid delivery rate of said pump where said gas detecting means senses the compressibility of the fluid within said pump to determine the presence of said gas where said gas is compressible and said liquid is not.

2. Apparatus as in claim 1 where said gas detecting means senses the compressibility of the fluid within said pump to determine the presence of said gas where said gas is compressible and said liquid is not.

3. Apparatus as in claim 1 where said gas detecting means senses the internal pressure and internal volume of said pump to determine said compressibility.

4. Apparatus as in claim 3 where said gas detecting means includes means responsive to change of said internal pump pressure with respect to change of said internal pump volume to determine said compressibility.

5. Apparatus as in claim 1 including means for cyclicly operating said pump and where said pump includes means for restraining the flow of said liquid in or out of said pump for at least a predetermined portion of each pump cycle.

6. Apparatus as in claim 5 where said gas detecting means detects said gas during said predetermined portion of each pump cycle.

7. Apparatus as in claim 6 where said pump is a piston pump.

8. Apparatus as in claim 7 where said gas detecting means senses the internal pressure and internal volume of said pump to determine said compressibility.

9. Apparatus as in claim 8 where said gas detecting means senses the position of the piston of said piston pump to determine said internal pump volume.

10. Apparatus as in claim 8 where said gas detecting means includes means responsive to change of said internal pump pressure with respect to change of said internal pump volume to determine said compressibility.

11. Apparatus as in claim 10 including means for establishing a predetermined level of detected gas which may undesirably affect the said liquid delivery rate of said pump.

12. Apparatus as in claim 11 including indicating means responsive to said gas for detecting means indicating that the level of detected gas exceeds said predetermined level.

13. Apparatus as in claim 11 including means for setting said pump to operate at a predetermined liquid delivery rate and control means responsive to said gas detecting means for controlling said pump to operate it at said predetermined liquid delivery rate in spite of the presence of said gas within the pump.

14. Apparatus as in claims 12 or 13 where said gas detecting means includes means for generating pulses proportional to the position of the piston of the piston pump and means for counting the number of pulses that occur during a predetermined change of said internal pump pressure to determine said compressibility.

15. Apparatus as in claim 14 where said indicating means is responsive to a predetermined count in said counting means to indicate when said level of detected gas exceeds said predetermined level.

16. Apparatus as in claim 14 where said control means is responsive to at least one predetermined count in said counting means to operate said pump at its predetermined delivery rate.

17. Apparatus as in claim 1 including means for establishing a predetermined level of detected gas which may undesirably affect the said liquid delivery rate of said pump.

18. Apparatus as in claim 17 including indicating means responsive to said gas detecting means indicating that the level of detected gas exceeds said predetermined level.

19. Apparatus as in claim 17 including means for setting said pump to operate at a predetermined liquid delivery rate and control means responsive to said gas detecting means for controlling said pump to operate it at said predetermined liquid delivery rate in spite of the presence of said gas within the pump.

20. Apparatus as in claims 18 or 19 where said gas detecting means includes means for generating pulses proportional to the position of the piston of the piston pump and means for counting the number of pulses that occur during a predetermined change of said internal pump pressure to determine said compressibility.

21. Apparatus as in claim 20 where said indicating means is responsive to a predetermined count in said counting means to indicate when said level of detected gas exceeds said predetermined level.

22. Apparatus as in claim 20 where said control means is responsive to at least one predetermined count in said counting means to operate said pump at its predetermined delivery rate.

23. Apparatus as in claim 1 including means for establishing a predetermined level of internal pump pressure corresponding to a pump outlet occlusion and means for detecting that the pressure within said pump has exceeded said predetermined level.

24. Apparatus as in claim 1 including means for establishing a predetermined level of internal pump pressure corresponding to a lack of liquid being supplied to said pump and means for detecting that the pressure within said pump is less than said predetermined value.

* * * * *